United States Patent
Pan et al.

(10) Patent No.: US 8,911,727 B2
(45) Date of Patent: Dec. 16, 2014

(54) MONOCLONAL ANTIBODY AGAINST HUMAN NON-SMALL CELL LUNG CARCINOMA AND USE THEREOF

(76) Inventors: Shiyang Pan, Nanjing (CN); Peijun Huang, Nanjing (CA); Fang Wang, Nanjing (CN)

( * ) Notice: Subject to any disclaimer, the term of this patent is extended or adjusted under 35 U.S.C. 154(b) by 0 days.

(21) Appl. No.: 13/977,881

(22) PCT Filed: Jan. 12, 2012

(86) PCT No.: PCT/CN2012/070279
§ 371 (c)(1),
(2), (4) Date: Jul. 1, 2013

(87) PCT Pub. No.: WO2013/063874
PCT Pub. Date: May 10, 2013

(65) Prior Publication Data
US 2014/0234327 A1    Aug. 21, 2014

(30) Foreign Application Priority Data
Nov. 3, 2011 (CN) .......................... 2011 1 0344683

(51) Int. Cl.
*A61K 39/395* (2006.01)
*C07K 16/18* (2006.01)
*C07K 16/30* (2006.01)
*C12N 5/16* (2006.01)
*G01N 33/574* (2006.01)

(52) U.S. Cl.
CPC ............. *C07K 16/18* (2013.01); *C07K 16/3023* (2013.01); *C12N 5/163* (2013.01); *G01N 33/57423* (2013.01); *A61J 2039/505* (2013.01); *C07K 2317/73* (2013.01)
USPC ...................................... 424/133.1; 530/387.3

(58) Field of Classification Search
None
See application file for complete search history.

(56) References Cited

FOREIGN PATENT DOCUMENTS

CN    201110377683.9    *    5/2012

* cited by examiner

*Primary Examiner* — Sheela J Huff
(74) *Attorney, Agent, or Firm* — CBM Patent Consulting, LLC

(57) ABSTRACT

The invention discloses a monoclonal antibody against human non-small cell lung carcinoma and a use of the monoclonal antibody. The monoclonal antibody is secreted by a hybridoma cell strain which is deposited as CCTCC Access Number No.: C201172. It has high yield and high titer, and has specific reactivity against lung adenocarcinoma and squamous carcinoma cell lines. Therefore, the monoclonal antibody may be applied in preparing drugs for treating human non-small cell lung carcinoma.

4 Claims, 10 Drawing Sheets

MONOCLONAL ANTIBODY AGAINST HUMAN NON-SMALL CELL LUNG CARCINOMA AND USE THEREOF

TECHNICAL FIELD

The invention relates to a monoclonal antibody against human Non-small Cell Lung Carcinoma (NSCLC) and application of the monoclonal antibody, belonging to the technical field of biotechnology.

BACKGROUND OF THE INVENTION

As the most common malignant tumor worldwide, lung cancer has the highest morbidity and mortality when compared with other malignant tumors. Lung cancer has become one of the serious diseases threatening the health and lives of human being. The traditional treatment methods have unsatisfactory therapeutic effect on lung cancer. Surgical treatment is helpless for multiple, metastatic or recurrent lung cancer patients, with easy recurrence. Chemotherapy has poor therapeutic effects for quite a number of patients and will result in serious side effects. Due to restrictions from important organs in the chest, radiotherapy also has limited therapeutic effect. In recent years, the targeted anti-tumor biotherapy has increasingly become a focus of research in the clinical treatment on lung cancer. While improving the therapeutic effect, the targeted anti-tumor biotherapy may also remarkably reduce the risk of side effects, so it is an important way for improving the therapeutic effect of lung cancer. At present, some lung cancer molecular targeted drugs have been developed. Although monoclonal antibodies targeting to EGFR, RAS, and some other gene mutations have been proofed and used for the treatment of lung cancer patients with a certain gene mutation, because of the incidence of these gene mutation is not high, saying EGFR mutation is about 30% for Asian population and only about 10% for European population, the clinical efficacy of such drugs in targeted lung cancer therapy still needs to be further enhanced. Therefore, discovery of more effective therapeutic targets and development of more effective targeted drugs with wide spectrum are of great significance to both diagnosis and therapy for lung cancer patients.

Lung cancer has a poor prognosis. The 5 years survival rate of lung cancer patients is lower than 15%. Among all lung cancer cases, Non-small Cell Lung Carcinoma (NSCLC) accounts for 80%-85%. The major cause for the poor prognosis of lung cancer is that early detection, diagnosis and further therapy are difficult for lung cancer. Monoclonal antibodies with specific reactivity against lung cancer may not only be used for tumor diagnosis and research, they also become a focus of the current pharmaceutical research in the aspect of tumor biotherapy. Although there are many researches[2-3] on monoclonal antibodies against lung cancer, few researches on screening of monoclonal antibodies against different targets of human lung cancer have been done.

SUMMARY OF THE INVENTION

The purpose of the invention is to provide a hybridoma cell strain secreting a monoclonal antibody against human non-small cell lung carcinoma, in view of the above defects of the prior art.

Another purpose of the invention is to provide a monoclonal antibody against human non-small cell lung carcinoma.

Still another purpose of the invention is to provide a use of the monoclonal antibody against human non-small cell lung carcinoma.

The purposes of the invention may be realized by the following technical solutions.

Provided in the invention is a hybridoma cell strain NM001-1 secreting a monoclonal antibody against human non-small cell lung carcinoma, deposited in China Center for Type Culture Collection on Aug. 31, 2011 with deposit no. in CCTCC: C201172.

Provided in the invention is a monoclonal antibody NJ001-1 against human non-small cell lung carcinoma, secreted by the hybridoma cell strain NM001-1 with deposit no. in CCTCC: C201172.

Provided in the invention is a use of the hybridoma cell strain with deposit no. in CCTCC: C201172 in preparing drugs for treating human non-small cell lung carcinoma.

Provided in the invention is a use of the hybridoma cell strain with deposit no. in CCTCC: C201172 in preparing detection reagents for diagnosis of human non-small cell lung carcinoma.

Provided in the invention is a use of the monoclonal antibody NJ001-1 in preparing drugs for treating human non-small cell lung carcinoma.

Provided in the invention is a use of the monoclonal antibody NJ001-1 in preparing detection reagents for diagnosis of human non-small cell lung carcinoma.

The invention has the following advantages.

In the invention, by using human lung adenocarcinoma cell line SPCA1 as immunogen and utilizing hybridoma technique, a hybridoma cell strain NM001-1 (CCTCC No.: C201172) capable of stably secreting a monoclonal antibody against human non-small cell lung carcinoma is screened out. The monoclonal antibody secreted by the hybridoma (CCTCC No.:C201172) has high yield and high titer, and has specific reactivity against lung adenocarcinoma and squamous carcinoma cell lines but no or low reactivity against benign tumor cell, normal lung cells, PBMCs from healthy people and some other common tumor cell lines (liver cancer, breast cancer and colon cancer). During immunohistochemical analysis, the monoclonal antibody NJ001-1 is positive for 31 cases of lung adenocarcinoma tissues and 24 cases of lung squamous carcinoma tissues (the NJ001-1 specific antigen expression rate is 100%), with lung adenocarcinoma tissue staining is tested strongly positive, but no reactivity against 20 cases of pulmonary inflammatory pseudotumor tissues. Of 16 cases of small cell lung cancer tissues, only 2 cases are tested weakly positive; and, of 16 cases of mammary carcinoma tissues, only 3 cases are tested weakly positive.

In the invention, researches have been done on the effects of the monoclonal antibody NJ001-1 on lung adenocarcinoma in vivo and in vitro by Soft Agar Colony Formation assays and a xenograft tumor model in nude mice. Results show that the monoclonal antibody NJ001-1 has remarkable inhibition on lung adenocarcinoma both in vivo and in vitro. In the invention, researches have been further done on the inhibition mechanism of the monoclonal antibody NJ001-1. Results show that the monoclonal antibody NJ001-1 inhibits the occurrence and development of tumors by induction of cell apoptosis and may be applicable to direct or assisted intervention in the therapy of lung cancer.

Figure 4:
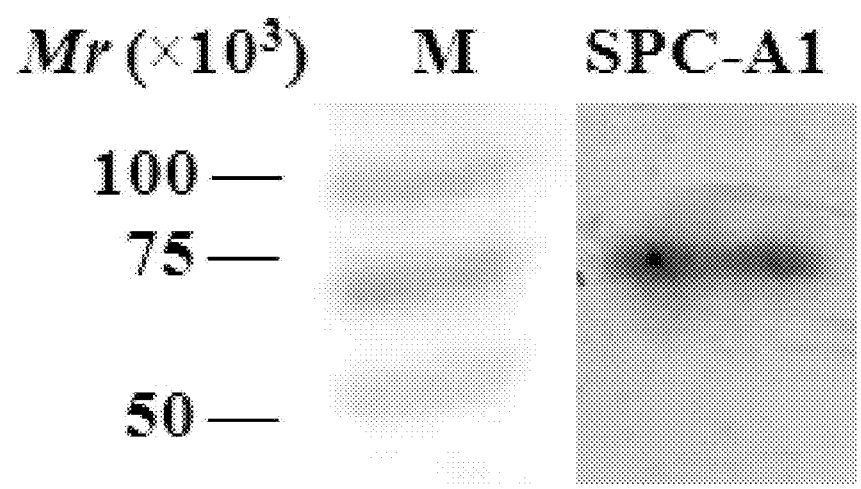
Figure 5:
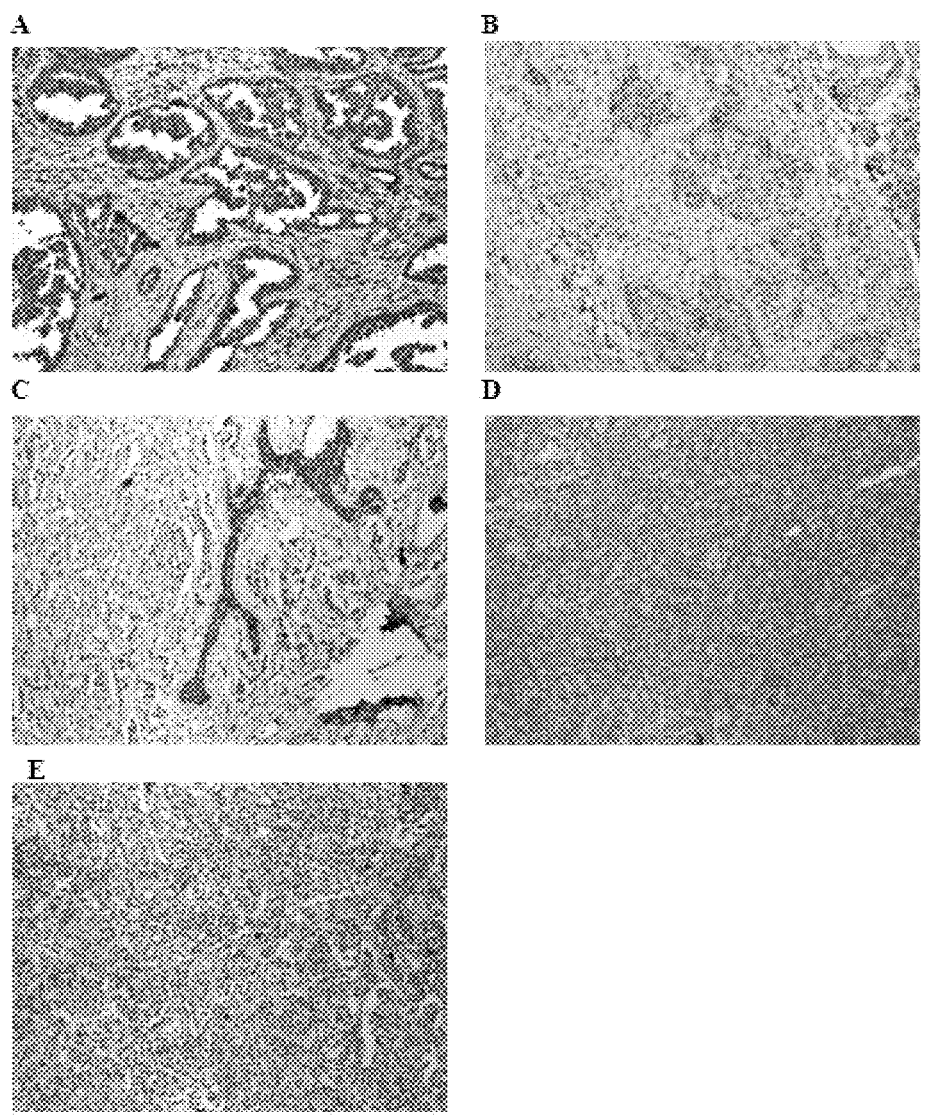
Figure 6:
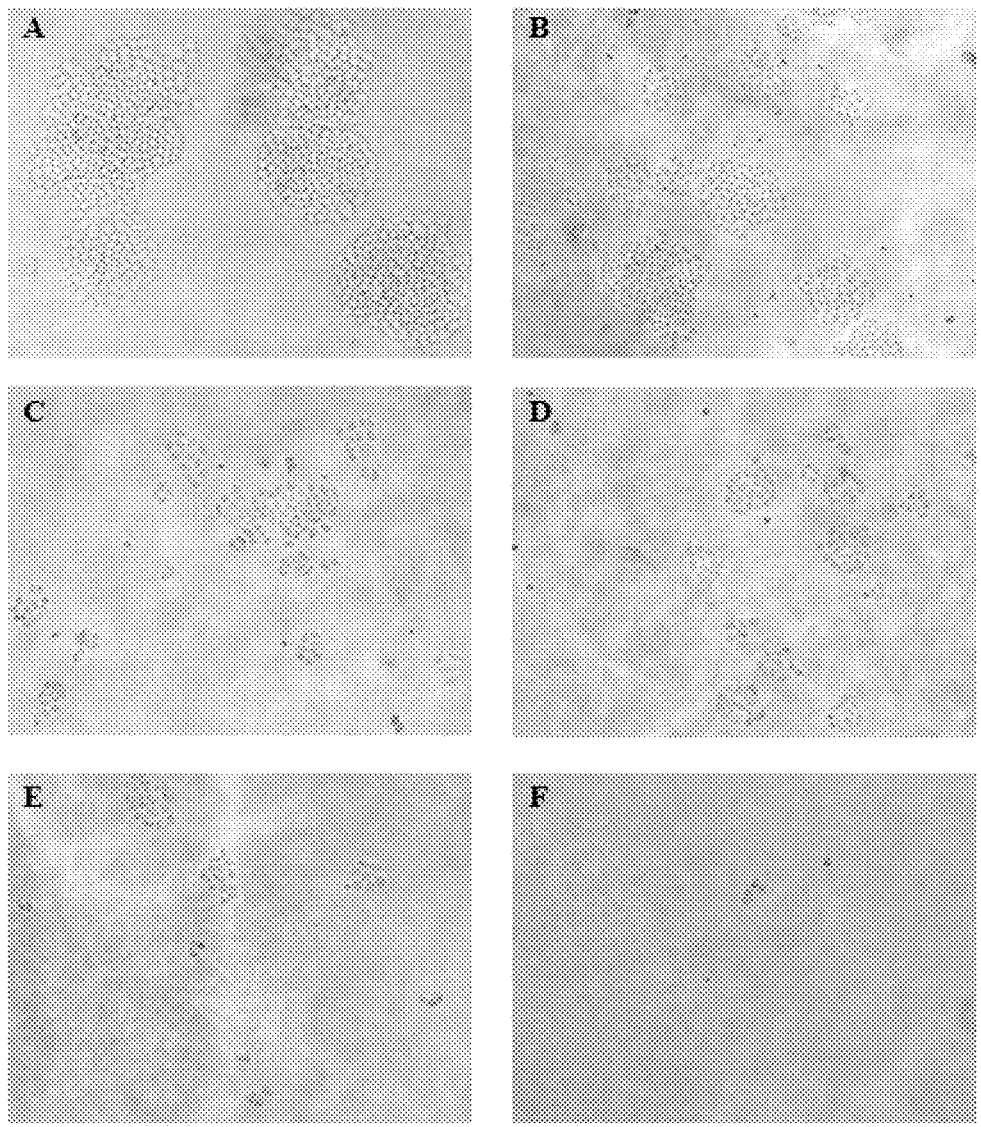
Figure 7:
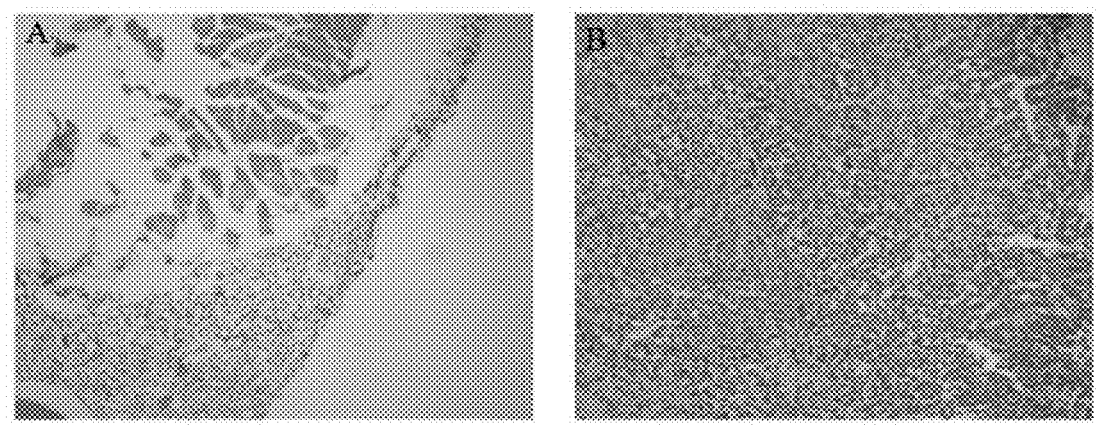
Figure 8:
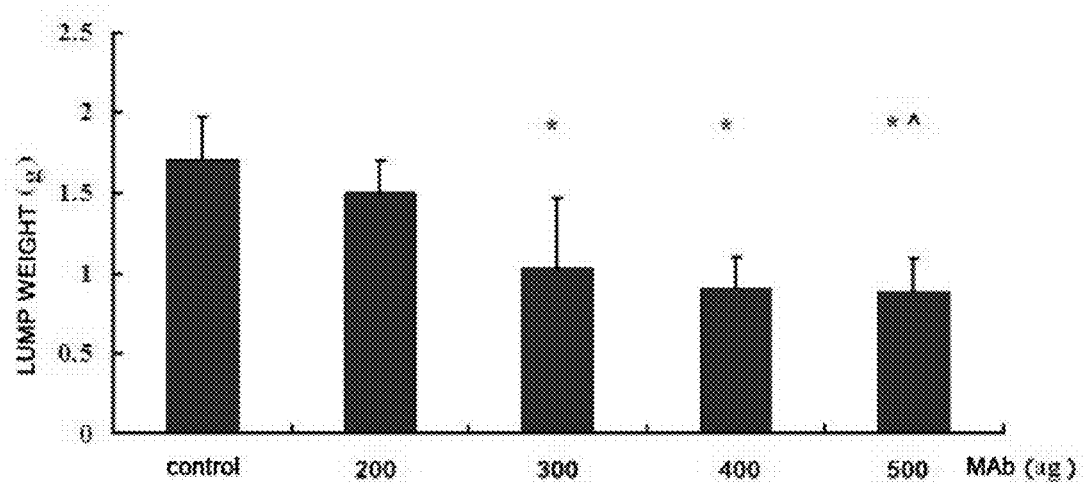
Figure 9:
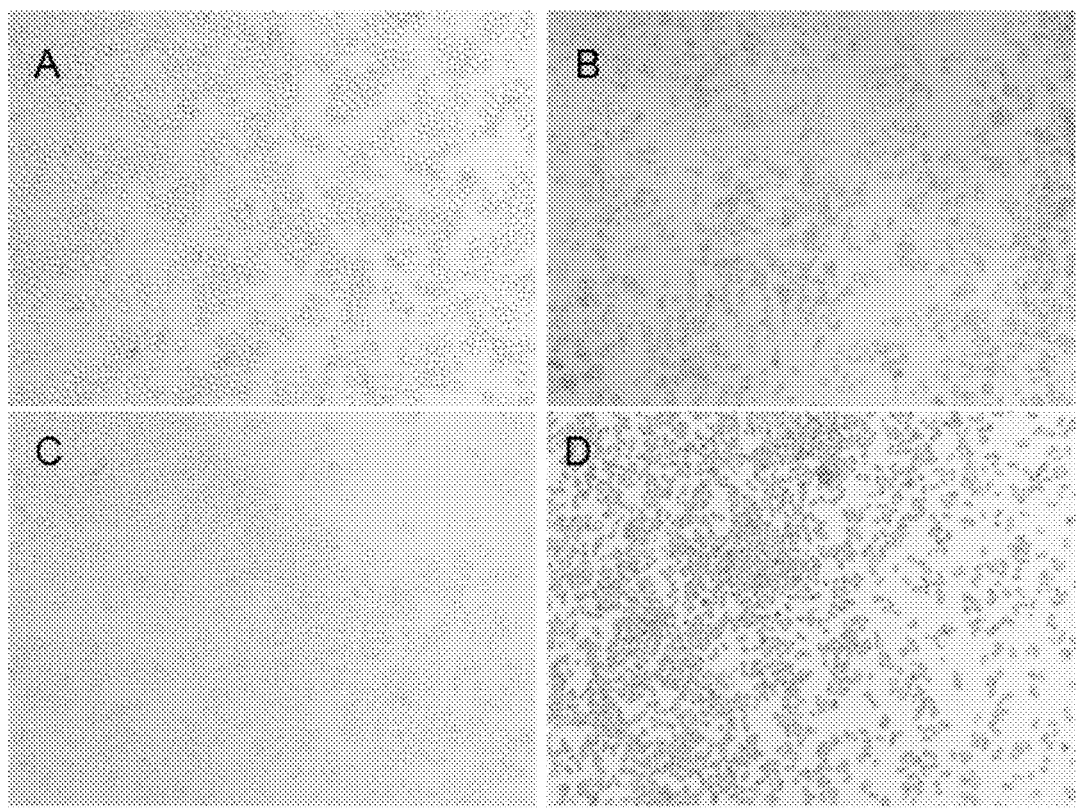
Figure 10:
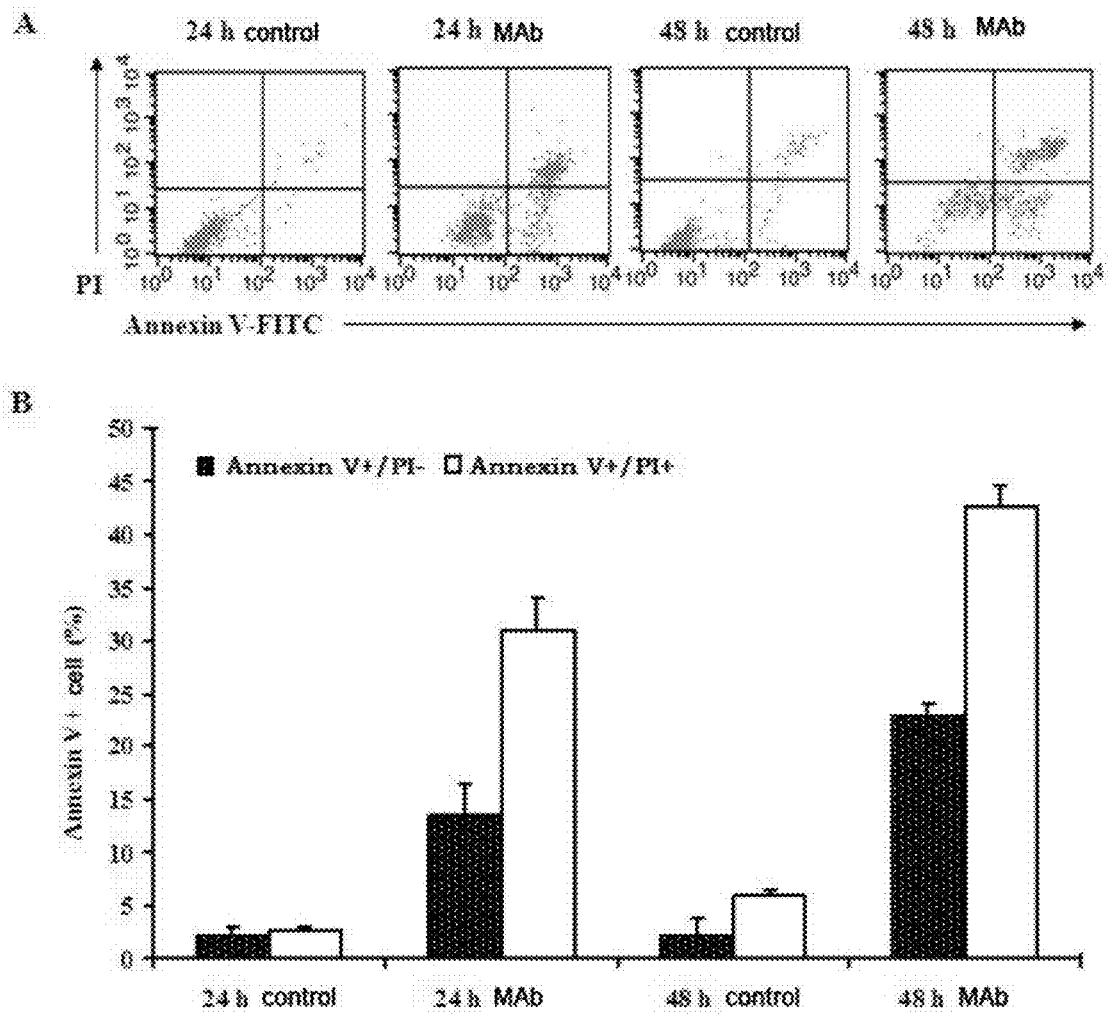

A: lung adenocarcinoma cell SPCA1; B: mammary carcinoma cell ZR-75-30; C: hepatocellular carcinoma cell HepG2; D: human embryonic lung fibroblast WI-38;

FIG. 4 shows Western blot analysis on the monoclonal antibody NJ001-1 and SPCA1 lysate;

FIG. 5 shows immunohistochemical analysis on reaction of the monoclonal antibody NJ001-1 with different pathological tissues (×200), where, A: non-small cell lung carcinoma (adenocarcinoma); B: non-small cell lung carcinoma (squamous carcinoma); C: mammary carcinoma; D: pulmonary inflammatory pseudotumor; E: small cell lung cancer;

FIG. 6 shows cloneies of SPCA1 formed on soft agar (×100), where, A-F refer to control group, and groups containing 100 μg/ml, 200 μg/ml, 300 μg/ml, 400 μg/ml and 500 μg/ml of monoclonal antibody NJ001-1, respectively;

FIG. 7 shows HE staining result of muscle tissues at the inoculated parts of nude mice (×200), where, A: a monoclonal antibody NJ001-1 incubation group: the HE staining result of muscle tissues at the inoculated parts; B: a control group: the HE staining result of tumor tissues at the inoculated parts;

FIG. 8 shows change of the tumor weight of the nude mice after treated by the monoclonal antibody NJ001-1, where, *$P<0.05$, compared with the control group; ^$P<0.05$, compared with the group containing 200 μg of monoclonal antibody;

FIG. 9 shows morphologic change of SPCA1 cells under the action of the monoclonal antibody NJ001-1 at different times (×100), where, A: control group, for 24 h; B: monoclonal antibody group, for 24 h; C: control group, for 48 h; D: monoclonal antibody group, for 48 h; and, FIG. 10 shows results of flow cytometry on the monoclonal antibody NJ001-1 inducing SPCA1 cell apoptosis, where, A: analysis diagrams of flow cytometry on the monoclonal antibody NJ001-1 inducing SPCA1 cell apoptosis, B: a statistical graph of flow cytometry analysis results on the monoclonal antibody NJ001-1 inducing SPCA1 cell apoptosis, Annexin $V^+/PI^-$ and Annexin $V^+/PI^+$ cell percentages representing early and late apoptosis rates, respectively.

INFORMATION ABOUT DEPOSIT OF SAMPLE OF BIOLOGICAL MATERIAL

Hybridoma cell strain NM001-1 was deposited on Aug. 31, 2011 under CCTCC Accession Number: C201172 in the China Center for Type Culture Collection having an office at Wuhan University, No. 299, Ba Yi Road, Wuhan, Hubei 430072, P. R. China (CN).

CCTCC deposits are made under the provisions of the Budapest Treaty on the International recognition of the Deposit of Microorganism for the Purpose of Patent Procedure and the Regulations thereunder (Budapest Treaty). The treaty assures maintenance of viable cultures for 30 years from the date of deposit. The hybridoma cell strain NM001-1 is available from CCTCC under the terms of the Budapest Treaty which assure permanent and unrestricted availability of progeny of the cell line to the public upon issuance of the pertinent U.S. patent application. The Budapest Treaty assures the availability of the cell line to one determined by U.S. Commissioner of Patents and Trademarks to be entitled thereto according to 35 U.S.C. §122 and the commissioner's rules pursuant thereto.

The assignee of the present application has agreed that if the cell line deposit should die, be lost or destroyed when cultivated under suitable conditions, it will be promptly replaced with viable specimen of the same cell line upon proper notification. Availability of a deposited cell line is not to be construed as a license to practice the invention in contravention of the rights granted under the authority of any government in accordance with its patent laws.

DETAILED DESCRIPTION OF THE INVENTION

1. Cells and Major Regents Involved in the Following Embodiments

Human non-small cell lung carcinoma (NSCLC) cell lines SPCA1, A549, NCI-H520 and NCI-H460, and other human cancer cell lines: liver cancer cell line HepG2, breast cancer cell line ZR-75-30, colon cancer line COL0205 and human embryonic lung fibroblast cell line WI-38 are all purchased from the cell bank of Chinese Academy of Sciences. SP2/0 mouse myeloma cell line is kept by the Laboratory; female BALB/c mice, 6 to 8 weeks old and 8 to 10 weeks old, are purchased from Shanghai Slyke Experimental Animals Company. RPMI 1640, DMEM, fetal bovine serum, 0.25% trypsin, polyethylene glycol, Hypoxanthine Thymidine (HT), Hypoxanthine Aminopterin Thymidine (HAT) and paraffin oil are all purchased from American Gibco Invitrogen Company. Horseradish Peroxidase (HRP) labeled goat-anti-mouse IgG, FITC labeled goat-anti-mouse IgG and soluble single-component TMB substrate solution are all purchased from Beijing Tiangen Company. Mouse Ig subclass assay kit is purchased from American Santa Cruz Company. Western blot developer is purchased from American Cell Signaling Company. Pulmonary inflammatory pseudotumor tissues, lung cancer tissues and mammary carcinoma tissues are provided by the Department of Pathology, Jiangsu People's Hospital. Model 550 type ELISA Reader is purchased from Bio-Rad Company. RPMI 1640 and fetal calf serum are purchased from the Company. Agarose is purchased from Promega Company. Annexin V-FITC cell apoptosis assay kit is purchased from Keygen Biotechnology Co., Ltd.

2. Cell Culture Methods Involved in the Following Embodiments

The above cells respectively grow in DMEM or RPMI 1640 culture medium containing 100 U/mL of 10% fetal bovine serum, 100 U/mL of penicillin and 100 U/mL of streptomycin, and are then cultured in a constant temperature incubator at 37° C. with 5% $CO_2$. Human Peripheral Blood Mononuclear Cells (PBMC) are obtained from healthy blood donors, and separated with conventional lymphocyte separation medium.

3. Statistical Analysis

Statistical analysis is performed on data with SPSS 16.0 statistical software. Fisher's Exact Propability is employed for inter-group comparison of qualitative data, and the variance has statistical significance when $P<0.05$. One-way analysis of variance is employed for inter-group comparison of quantitative data. LSD is employed for multiple comparisons of homogeneous variance, and the variance has statistical significance when $P<0.05$. Dunnett's C is employed for multiple comparisons of non-homogeneous variance, 0.05 regarded as a significance level during multiple comparisons.

Embodiment 1

Obtainment of Hybridomas 1.1. Animal Immunization

Female BALB/c mice, 6 to 8 weeks old, are prepared and then abdominally injected for the purpose of immunization for four times with $2\times10^6$ SPCA1 cells injected each time, once every 3 weeks. Blood is collected from the inner canthus of the mice before each immunization, and the titer of the serum antibody of the mice is detected by indirect cell ELISA. Mice splenocytes are prepared for fusion when the titer of the serum antibody of the immunized mice reaches the maximum value and will not rise any more, and the mice splenocytes will be immunized once 3 days before fusion.

1.2. Indirect Cell ELISA Tests

SPCA1 cells are inoculated on a 96-well plate with $2\times10^5$ cells for each well until the cell growth reaches 80% fusion, fixed with 95% ethanol, washed with PBS for 3 times, soaked in 0.2% Triton-X-100 for 20 min, and then sealed with 50 g/L of BSA at 37° C. for 2 h, sequentially added with 100 µL of immunized mice serum in different concentrations, incubated at 37° C. for 1 h, washed with PBS for 3 times, added with 100 µL of HRP labeled goat-anti-mouse IgG which is diluted in a ratio of 1:1000, incubated at 37° C. for 45 min, washed with PBS, added with TMB developer, and finally incubated at 37° C. for 10 min, so far, the reaction is stopped. The optical density (OD) for 450 nm is detected by an ELISA Reader, by using non-immunized mice serum (1:1000) as negative control.

1.3. Cell Fusion

The spleen of the immunized mice is prepared and grinded into cell suspension. The cell suspension is fused with myeloma cells SP2/0 in the logarithmic growth phase (Yao Xiaoling, Liu Xiaoyan, Wu Qiang et al. *Preparation of Human Lung Cancer Related Monoclonal Antibody and Purification of Its Antigen* [J]. Chinese Journal of Immunology, 2006, 22 (12): 1140-1145.). 960 wells are fused at first, cell clones appear after one week of fusion, and there are 800 wells grown with hybridoma cells, so the fusion rate is about 83%. Indirect cell ELISA tests are carried out in accordance with the method mentioned in 1.2 to screen positive hybridoma cells (the immunized mice serum in the indirect cell ELISA tests mentioned in 1.2 is replaced with hybridoma cell culture supernatant), and the positive hybridoma cells are then inoculated and sub-cloned by limited dilution for 4 times to obtain two highest positive hybridoma cell strains NM001-1 and NM001-2 capable of secreting SPCA1 monoclonal antibody stably.

Embodiment 2

Preparation and Purification of Monoclonal Antibody Ascites

Female BALB/c mice, 8 to 10 weeks old, are prepared and then abdominally injected with 0.5 mL of paraffin oil, and after 10 days, abdominally injected with well-grown hybridoma cells NM001-1 and NM001-2, about $1\times10^6$ hybridoma cells for each mouse, respectively. Ascites is pumped after 1 to 2 weeks. The ascites is risen to 37° C. for 1 h and then kept overnight at 4° C.; and, centrifuged the next day, and purified by Protein G affinity chromatography to obtain the purified monoclonal antibodies NJ001-1 and NJ001-2.

Embodiment 3

Identification of Monoclonal Antibodies 3.1 Identification of Subclass of Monoclonal Antibodies Ig The purified monoclonal antibodies are diluted with PBS in a rate of 1:10000 in accordance with Instructions of Assay Kit. The subclasses of the monoclonal antibodies NJ001-1 and NJ001-2 are IgG, and the light chain is K chain.

3.2 Measurement of Titer of Monoclonal Antibodies

The purified monoclonal antibodies NJ001-1 and NJ001-2 are diluted in multiple proportion with PBS, respectively, and 100 µL of the diluted solution is measured and added to a 96-well plate coated with SPCA1 cells, the optical density (OD) is measured by indirect cell ELISA, and the maximum dilution of the monoclonal antibodies which may have immune response to the coating cells is regarded as the titer. The titer of the monoclonal antibody NJ001-1 is $4\times10^6$, and the titer of the monoclonal antibody NJ001-2 is $1.6\times10^6$. The hybridoma cell strain NM001-1 is deposited in China Center for Type Culture Collection on Aug. 31, 2011, with CCTCC No.: C201172, addressed: Wuhan University, Wuhan City, China.

3.3 Identification of Chromosomes

Figure 1:
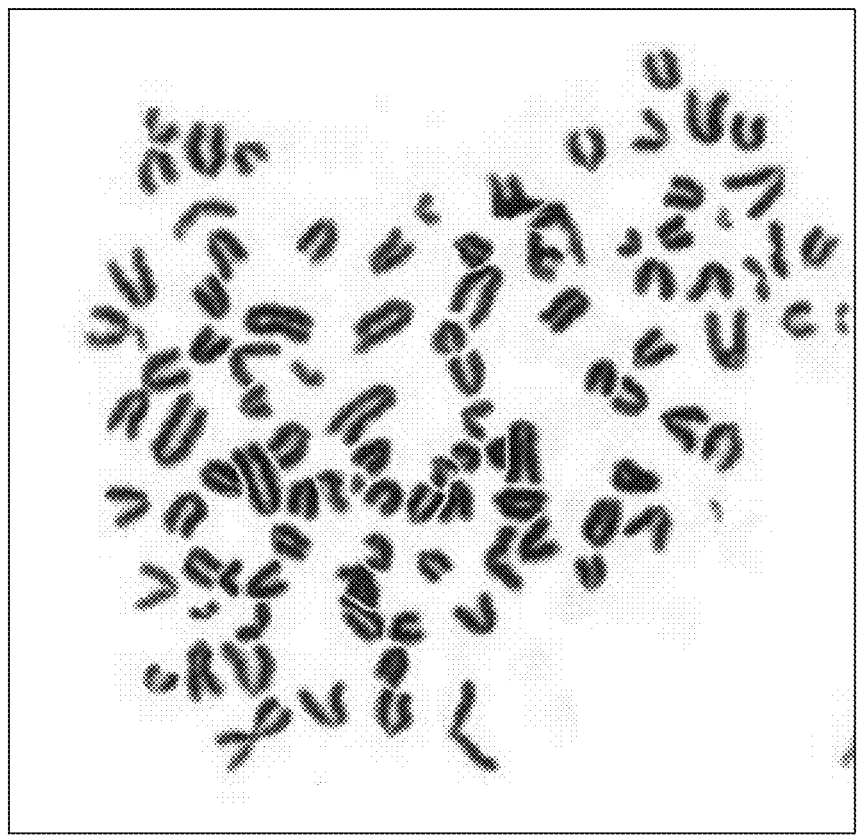
FIG. 1 is an analysis diagram of chromosomes of a hybridoma cell NM001-1 secreting a monoclonal antibody NJ001-1.

The hybridoma cells NM001-1 in the logarithmic growth phase are treated with colchicine for 8 h. Then, the cells are collected, centrifugally thrown on a slide, treated with 0.075 mol/L of KCl in hypotonic manner, fixed with methanol-glacial acetic acid stationary liquid, and then stained with 10% Giemsa for 10 min. Finally, chromosomes are detected by a microscope. The number of chromosomes of the hybridoma cell is within 100-106, this is because the number of chromosomes of the mice cells is 40 while the number of chromosomes of cells SP2/0 is within 62-68 in average. It is proved that the chromosomes in the hybridoma cells come from the spleen cells of the immunized mice and myeloma cells SP2/0; and all the chromosomes belong to the chromosome karyotype of the hybridoma cells, referring to FIG. 1.

3.4 Identification of Specificity of Monoclonal Antibodies

Figure 2:
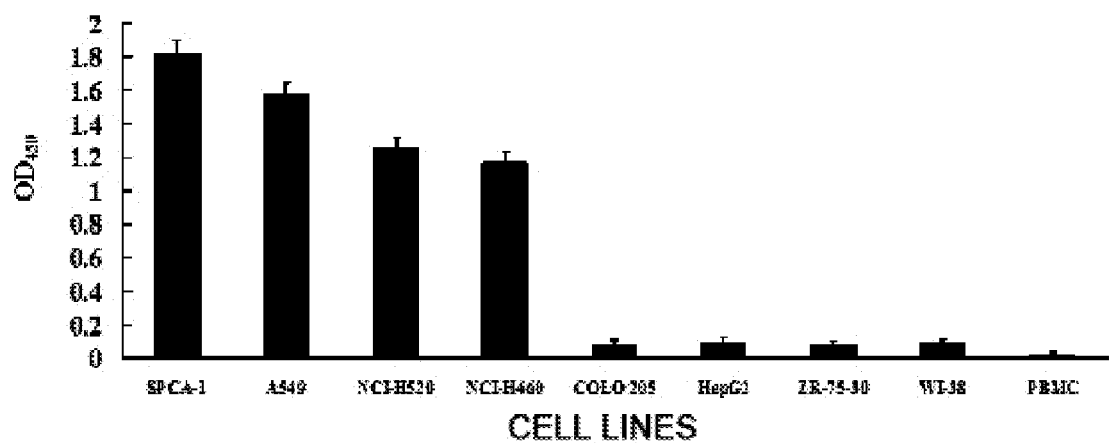
FIG. 2 shows analysis on reactivity of the monoclonal antibody NJ001-1 against various kinds of tumor cells and non-tumor cells by indirect cell ELISA.

Indirect cell ELISA analysis is carried out for the purified monoclonal antibody NJ001-1 with the above 9 kinds of cell lines and the PBMCs from healthy people, respectively, to observe whether a positive response occurs. The results show that the monoclonal antibody NJ001-1 has strong response to antigens of the lung cancer cells (SPCA1, A549, NCI-H520, NCI-H460) only, and no response to antigens of other tumor cells (HepG2, Colo 205, ZR-75-30), antigens of normal human embryo lung cells (WI-38) and PBMCs from healthy people (referring to FIG. 2).

Embodiment 4

Indirect Immunofluorescence Assay

Figure 3:
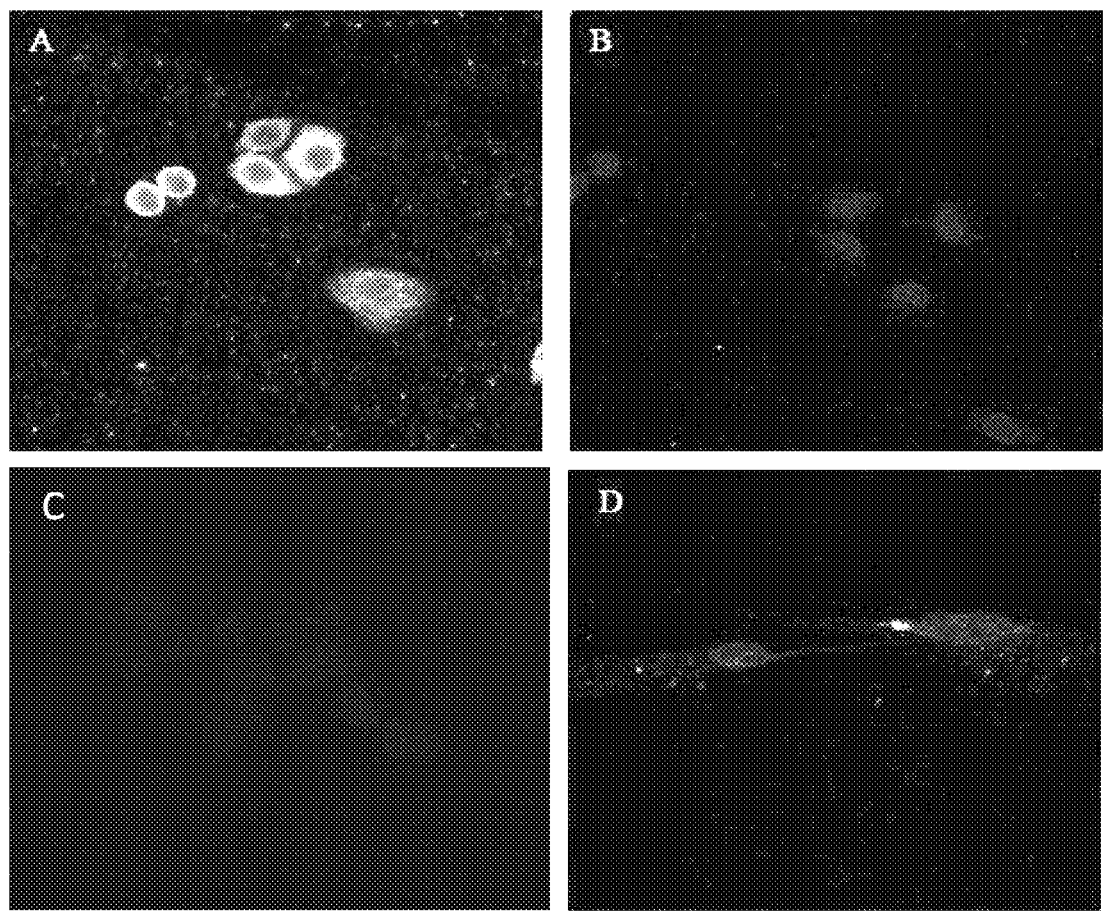
FIG. 3 shows indirect immunofluorescence reaction results of the monoclonal antibody NJ001-1 (×400), where, blue fluorescence: Hoechst nuclear staining result; green fluorescence: FITC labeled second antibody staining result.

A sterile cover slide is placed in a 6-well plate, and the above cell lines are cultured in the plate. The cover slide is taken out when the cells grow adhering to the wall. The cells are fixed in the plate with 95% ethanol. The cells in the plate are washed with PBS for 3 times, soaked in 0.2% Triton-X-100 for 20 min, and then sealed with 50 g/L of BSA at 37° C. for 2 h; added with the purified monoclonal antibody NJ001-1 diluted in a rate of 1:1000, and incubated at 37° C. for 1 h; washed with PBS for 5 times, added with FITC labeled goat-anti-mouse IgG diluted in a rate of 1:80, incubated at 37° C. for 1 h, washed with PBS, stained with Hoechst for 10 min, washed with PBS, sealed with glycerol, and observed by an LSM710 confocal scanning laser microscope (Germany Zeus Company). The results are as shown in FIG. 3. From FIG. 3, it can be seen that the monoclonal antibody NJ001-1 has strong response to antigen of SPCA1 cells only, that is, obvious yellowish green fluorescence can be seen on the cell membrane of the monoclonal antibody, which indicates that the antigen identified by the monoclonal antibody NJ001-1 is on the cell membrane. The monoclonal antibody NJ001-1 has no response to ZR-75-30, HepG2 and WI-38, as there is no green fluorescence appeared.

Embodiment 5

Detection of Specific Identification of Antigens of Monoclonal Antibodies by Western Blot The SPCA1 cell lysate is treated by SDS-PAGE electrophoresis, transferred to a nitrocellulose membrane, sealed in 50 g/L of skim milk at room temperature for 2 h, added with the monoclonal antibody NJ001-1 diluted in a rate of 1:300, kept overnight at 4° C., washed with PBS-T for 3 times, added with HRP labeled goat-anti-mouse IgG diluted in a rate of 1:1000, incubated at 37° C. for 45 min, and finally developed by ECL luminescent liquid. Western blot results show that a clear stripe with a molecular weight of 70000 may be seen on the film, referring to FIG. 4.

Embodiment 6

Immunohistochemistry

Human inflammatory pseudotumor tissues, lung adenocarcinoma tissues, lung squamous carcinoma tissues, small cell lung cancer tissues and mammary carcinoma tissues are prepared, and then embedded with paraffin, and finally sliced. The purified monoclonal antibody NJ001-1 serves as the primary antibody and the serum of the SPCA1 immunized mice serves as the positive control of the primary antibody, and PBS is used for replacing the primary antibody and the secondary antibody as negative control. Antigen retrieval is carried out by boiling. The tissues are developed with the developer from Cell Signaling Company, after-stained with hematoxylin, and observed by microscope. The results of immunohistochemistry are as shown in Table 1. The monoclonal antibody NJ001-1 has strong response to antigens of lung adenocarcinoma tissues and lung squamous carcinoma tissues, and the corresponding antigens identified by the monoclonal antibody NJ001-1 are mainly distributed on the cell membrane of the cells in lung cancer tissues. However, the monoclonal antibody NJ001-1 has no response or weak response to small cell lung cancer tissues, inflammatory pseudotumor tissues and mammary carcinoma tissues, referring to FIG. 5. The cell membrane antigen expression percentage of the non-small cell lung cancer tissues with the small cell lung cancer tissues has significant difference ($P<0.001$); the cell membrane antigen expression percentage of the non-small cell lung carcinoma tissues with the inflammatory pseudotumor tissues and the mammary carcinoma tissues also has statistical differences ($P<0.001$, $P<0.001$); and the antigen expression percentage of the lung adenocarcinoma tissues and the lung squamous carcinoma tissues has no difference, but the staining intensity of the lung squamous carcinoma tissues is slightly lower than that of the lung adenocarcinoma tissues.

TABLE 1

Results of immunohistochemistry on response of monoclonal antibody NJ001-1 with different pathological tissues

| Type | Positive rate (Positive cases/Example cases) | Staining intensity |
| --- | --- | --- |
| Non-small cell lung carcinoma (Adenocarcinoma) | 100% (31/31) | +++ |
| Non-small cell lung carcinoma (Squamous carcinoma) | 100% (24/24) | ++ or +++ |
| Small cell lung cancer | 12.50% (2/16) | − to + |
| Inflammatory pseudotumor | 0% (0/20) | − |
| Mammary carcinoma | 18.75% (3/16) | − to + |

Remarks: "−" refers to negative; "+" refers to weakly positive; "++" refers to moderately positive, and "+++" refers to strongly positive.

Embodiment 7

Soft Agar Clone Formation Assay

Agarose solution in a concentration of 3% is prepared with physiological saline and sterilized by high pressure steam. Two layers of gel agar (Hong K W, Kim C G, Lee S H, et al. *A Novel Anti-EGFR Monoclonal Antibody Inhibiting Tumor Cell Growth by Recognizing Different Epitopes from Cetuximab [J]*. J Biotechnol, 2010, 145 (1):84-91.) are prepared in a 6-well cell culture plate. The bottom layer is a supporting layer. RPMI 1640 complete medium containing 10% fetal bovine serum is mixed with 3% agarose in a rate of 5:1 and prepared into a culture medium containing 0.5% agar. The culture medium is added to the 6-well hole with 2 mL for each well, cooled and solidified at room temperature. SPCA1 in the logarithmic growth phase is collected and prepared into single cell suspension with the complete medium which is then kept at 37° C. A proper amount of single cell suspension is fully mixed with 3% agarose solution and monoclonal antibody NJ001-1 solutions in different concentrations, and added to the plate with 2 mL for each well to be prepared into superstratum agar containing 3% agarose. Each well contains $2\times10^4$ cells, the final concentrations of the antibody are 0 μg/mL, 100 μg/mL, 200 μg/mL, 300 μg/mL, 400 μg/mL, 500 μg/mL, 1000 μg/mL and 2000 μg/mL, respectively, and three parallel samples are provided for each dose is. After the agar is solidified at room temperature, the culture plate is put into an incubator to be cultured at 37° C. with 5% $CO_2$ for two weeks. The culture plate is upside down put on a microscope for counting, a colony with not less than 50 cells is defined as a clone, and the clone formation rate and the inhibition rate are calculated: clone formation rate=(number of clones/number of the inoculated cells)×100%; and inhibition rate=(1-clone formation rate of the monoclonal antibody group/clone formation rate of the control group)×100%. The assay will be repeated for 3 times.

The soft agar clone formation assay shows that the monoclonal antibody NJ001-1 may effectively inhibit the clone formation of lung adenocarcinoma SPCA1 in the soft agar, and the inhibition effect thereof is positively proportional to the concentration of the antibody (Table 2). The colonies formed by cells under the action of the monoclonal antibody NJ001-1 are reduced obviously, far less than those of the control group. Part of cells may not grow in the soft agar to form a colony, and are dispersed as single cells (referring to FIG. 6).

TABLE 2

Effect of monoclonal antibody NJ001-1
on SPCA1 clone formation in soft agar

| Concentration of antibody (μg/mL) | Number of Clones (not less than 50 cells/clone) | Clone formation rate (%) | Clone inhibition rate (%) |
|---|---|---|---|
| 0 | 192 ± 7.07 | 0.96 | 0 |
| 100 | 146 ± 12.73 | 0.73 | 23.96 |
| 200 | 119 ± 8.19 | 0.60 | 38.02 |
| 300 | 70 ± 4.24 | 0.35 | 63.54 |
| 400 | 33 ± 6.09 | 0.17 | 82.81 |
| 500 | 0 | 0 | 100 |
| 1000 | 0 | 0 | 100 |
| 2000 | 0 | 0 | 100 |

Embodiment 8

Experiment of Xenograft Tumor Model in Nude Mice 8.1 Preliminary Experiment in Nude Mice $2 \times 10^6$ SPCA1 cells and the monoclonal antibody NJ001-1 are incubated at 37° C. for 2 h, and then subcutaneously inoculated into the right axillae of 5 nude mice, to establish a monoclonal antibody incubation group. In the control group, a same amount of SPCA1 cells without treatment of the monoclonal antibody NJ001-1 are inoculated to the same inoculated parts of 5 nude mice. Three weeks later, the mice are sacrificed, and then dissected. The nude mice in the monoclonal antibody incubation group all have no lump visible to the naked eyes in the inoculated parts, but the nude mice in the control group have apparent lumps in the inoculated parts. Tissues are collected from the inoculated parts of the nude mice in the monoclonal antibody incubation group and of the nude mice in the control group, respectively, and then fixed with 10% formaldehyde, embedded with paraffin, sliced, and stained with conventional HE, and finally put on the microscope for observation of pathological change. The results are as shown in FIG. 7. HE staining shows that the muscular tissues from the inoculated parts of the nude mice in the monoclonal antibody incubation group have no tumor cell grown, while pathological section staining shows that the tissues from lumps of the nude mice in the control group have histological characteristics of malignant tumors.

8.2. Experiment of Xenograft Tumor Model in Nude Mice

Another 25 nude mice are randomly divided into 5 groups, respectively, i.e.: control group without treatment of the monoclonal antibody NJ001-1 (control group, for short), and 200 μg, 300 μg, 400 μg and 500 μg groups with treatment of the monoclonal antibody NJ001-1 (monoclonal antibody groups, for short), with 5 mice in each group. $2 \times 10^6$ SPCA1 cells are subcutaneously inoculated into the right axilla of each of the nude mice, with 200 μL for each mouse. The mice in the monoclonal antibody groups, are treated with the monoclonal antibody from the day of inoculation. The mice in the monoclonal antibody groups are abdominally injected with 200 μL of monoclonal antibody solutions in different concentrations (containing 200 μg, 300 μg, 400 μg and 500 μg of monoclonal antibody NJ001-1, respectively). The mice are injected once every day in former 5 days, and then once every 4 days, consecutively for 2 weeks (total 9 times). In the control group, the monoclonal antibody solution for the monoclonal antibody groups is replaced by a same volume of physiological saline, while the injection time and the injection way are the same as those for the monoclonal antibody groups. Daily activities, mental condition, eating condition and lump occurrence time of the mice are observed and recorded every day. Once subcutaneous nodules appear, the long diameter (a) and the short diameter (b) of the transplanted tumor are measured by a vernier caliper, and the volume of the transplanted tumor $V=ab^2/2^{[8]}$. At the end of treatment, the mice are sacrificed, and then dissected to separate and weigh the tumor so as to calculate the tumor inhibition rate: tumor inhibition rate=(1−Average tumor weight of monoclonal antibody group/Average tumor weight of control group)×100%.

The SPCA1 cells are subcutaneously inoculated to the nude mice, and then the nude mice are abdominally injected with physiological saline and different doses of monoclonal antibodies NJ001-1 for 3 weeks. 9 days later, nodules visible to the naked eyes appear in the inoculated parts, and the tumor formation rate is 100%. From the 13th day, the volume of the tumor is measured till the 21st day. It is found that, form the 17th day, the volume increase rate of the tumor in the 300 μg, 400 μg and 500 μg monoclonal antibody groups is obviously reduced when compared with the control group, and the difference lasts till the end of the experiment (P=0.004, P=0.003, P=0.003, Table 3). At the end of treatment, the tumor is separated and the lumps are weighed. The results are as shown in FIG. 8. The average tumor weights of the mice in the control group and in the 200 μg, 300 μg, 400 μg and 500 μg monoclonal antibody groups are (1.71±0.27)g, (1.50±0.20)g, (1.03±0.44)g, (0.91±0.19)g and (0.88±0.21)g, respectively; the tumor weights of the mice in the four groups have statistical significance (F=4.303, P=0.043); the average tumor weights of the mice in the 300 μg, 400 μg and 500 μg monoclonal antibody groups are obviously lower than that in the control group (P=0.036, P=0.032, P=0.014); and the 200 μg monoclonal antibody group and the 500 μg monoclonal antibody group also have significant difference (P=0.043). The tumor inhibition rates in the 200 μg, 300 μg, 400 μg and 500 μg monoclonal antibody groups are 12.28%, 39.77%, 46.78% and 48.54%, respectively. The results show that the monoclonal antibody NJ001-1 may obviously inhibit the growth of the transplanted tumors of the lung adenocarcinoma.

TABLE 3

Volume change of tumor of nude mice with
treatment of monoclonal antibody NJ001-1

| | Tumor volume/mm³ | | |
|---|---|---|---|
| | 13th day | 17th day | 21st day |
| Control group | 327.48 ± 156.56 | 1687.24 ± 285.79 | 2978.49 ± 660.72 |
| 200 μg monoclonal antibody group | 193.35 ± 20.72 | 724.44 ± 103.50 | 1982.10 ± 849.04 |
| 300 μg monoclonal antibody group | 111.86 ± 30.62 | 405.90 ± 35.78 * | 1123.88 ± 51.54 * |
| 400 μg monoclonal antibody group | 103.45 ± 68.36 | 353.71 ± 120.02 * | 1058.15 ± 302.36 * |

TABLE 3-continued

Volume change of tumor of nude mice with treatment of monoclonal antibody NJ001-1

| | Tumor volume/mm$^3$ | | |
|---|---|---|---|
| | 13th day | 17th day | 21st day |
| 500 μg monoclonal antibody group | 98.53 ± 29.15 | 301.23 ± 57.65 * | 1013.62 ± 157.68 * |

* $P < 0.05$, compared with the control group.

Embodiment 9

Detection of Cell Apoptosis

The SPCA1 cells in the logarithmic growth phase are collected and then prepared into single cell suspension. The single cell suspension is added into a 12-well plate with $1 \times 10^5$ cells for each well and cultured overnight. The culture supernatant is discarded. The well plate is washed with D-Hank's solution with 500 μL for each well. For the antibody groups (a group for 24 h and a group for 48 h): 500 μL of monoclonal antibody NJ001-1 solution is added into each well, and the concentration of the monoclonal antibody is 300 μg/mL. For the control groups (a group for 24 h and a group for 48 h): 500 μL of culture medium is added into each well. The groups are cultured for 24 h and 48 h after intervention, respectively, and then upside down put on the microscope for observing and photographing. The results are as shown in FIG. 9. Cells are collected, and the cell apoptosis is detected by flow cytometry. Each group is provided with three parallel holes, and the experiment will be repeated for three times. The method for detecting the cell apoptosis by the flow cytometry is as follows: cells are digested with 0.25% pancreatin, and the cell suspension is centrifuged at 2000 rpm×5 min; the cells are washed with PBS for two times, and then collected, added with 500 μL of Binding Buffer cell suspension, added with 5 μL of Annexin V-FITC and mixed uniformly, and then added with 5 μL of Propidium Iodide and mixed uniformly, reacted at room temperature away from light for 5 min to 15 min, and observed and detected by the flow cytometry within 1 h: excitation wavelength Ex=488 nm, and emission wavelength Em=530 nm. The green fluorescence of Annexin V-FITC is detected by the FITC channel (FL1), and the red fluorescence of PI is detected by the PI channel (FL3). Annexin V$^+$/PI$^-$(%) and Annexin V$^+$/PI$^+$(%) respectively represent early and late apoptosis rates, and the total apoptosis rate is the sum of early and late apoptosis rates.

FIG. 9 shows that the cells in the control group are in normal morphology and vigorous growth. After 300 μg/mL of monoclonal antibody NJ001-1 takes effect on the SPCA1 cells for 24 h and 48 h, the cells gradually appear apoptosis changes, such as karyopyknosis and cytoplasm reduction, with obvious morphologic difference from those in the control group. The apoptosis detection results (referring to FIG. 10) show that the total apoptosis rates of the cells in the monoclonal antibody groups for 24 h and 48 h reach 45.36% and 69%, respectively, with obviously increase (P=0.001, P<0.001) when compared with the control group; and the total apoptosis rates of the cells in the monoclonal antibody groups for 24 h and 48 h have a statistical difference (P=0.003). The apoptosis rates in the late stage of the cells in the monoclonal antibody groups for 24 h and 48 h have significant difference (P=0.002, P=0.001) with those in the control group, and the apoptosis rate in the monoclonal antibody group for 48 h is obviously increased (P=0.004), when compared with that in the monoclonal antibody group for 24 h. The above results show that the apoptosis rate of the SPCA1 cells gradually increases with time, which indicates that the effect of the monoclonal antibody NJ001-1 on the induction of apoptosis of the SPCA1 is time dependent.

The invention claimed is:

1. A murine hybridoma deposited as CCTCC Accession Number C201172.
2. A monoclonal antibody produced by the murine hybridoma of claim 1.
3. The monoclonal antibody according to claim 2, wherein said monoclonal antibody specifically recognizes and binds a human non-small cell lung cancer cell.
4. A pharmaceutical composition comprising the monoclonal antibody of claim 2 and a pharmaceutically acceptable carrier.

* * * * *

UNITED STATES PATENT AND TRADEMARK OFFICE
CERTIFICATE OF CORRECTION

| | |
|---|---|
| PATENT NO. | : 8,911,727 B2 |
| APPLICATION NO. | : 13/977881 |
| DATED | : December 16, 2014 |
| INVENTOR(S) | : Pan et al. |

Page 1 of 1

It is certified that error appears in the above-identified patent and that said Letters Patent is hereby corrected as shown below:

<u>Title page</u>

Item 76 – Inventors:

"Peijun Huang, Nanjing (CA)" - should read "Peijun Huang Nanjing (CN)"

Signed and Sealed this
Fourteenth Day of April, 2015

Michelle K. Lee
*Director of the United States Patent and Trademark Office*